United States Patent [19]
Johnson

[11] Patent Number: 5,678,558
[45] Date of Patent: *Oct. 21, 1997

[54] DISPOSABLE BLOOD PRESSURE CUFF

[75] Inventor: David E. Johnson, Madison, Conn.

[73] Assignee: CAS Medical Systems, Inc., Branford, Conn.

[*] Notice: The term of this patent shall not extend beyond the expiration date of Pat. No. 5,511,552.

[21] Appl. No.: 556,050

[22] Filed: Nov. 13, 1995

Related U.S. Application Data

[63] Continuation of Ser. No. 300,396, Sep. 2, 1994, Pat. No. 5,511,552.
[51] Int. Cl.⁶ .................................................. A61B 5/022
[52] U.S. Cl. .................................... 128/686; 606/202
[58] Field of Search ................................. 128/686, 672, 128/677; 606/202

[56] References Cited

U.S. PATENT DOCUMENTS

| | | | |
|---|---|---|---|
| 2,582,123 | 1/1952 | Heitz | 128/686 |
| 3,120,846 | 2/1964 | Fletcher | 128/686 |
| 3,473,525 | 10/1969 | Hanafin | 128/686 |
| 3,659,592 | 5/1972 | Natkonski | 128/686 |
| 3,699,943 | 10/1972 | Hanafin | 128/686 |
| 3,756,239 | 9/1973 | Smythe | 128/686 |
| 3,760,795 | 9/1973 | Adelhed | 128/686 |
| 4,979,953 | 12/1990 | Spence | 128/686 |
| 5,228,448 | 7/1993 | Byrd | 128/686 |
| 5,392,782 | 2/1995 | Garrett | 128/686 |
| 5,396,894 | 3/1995 | Eide et al. | 128/686 |

*Primary Examiner*—Jennifer Bahr
*Assistant Examiner*—Bryan K. Yarnell
*Attorney, Agent, or Firm*—William W. Jones

[57] ABSTRACT

A disposable blood pressure cuff is made from a composite of a non-stretchable paper component and an elastic thermoplastic material component. The paper component provides the necessary outer circumferential strength for the cuff so that it will not stretch outwardly when it is inflated. The thermoplastic layer provides an inwardly expandable surface for contacting a limb of the patient which the cuff encircles. A tape tab is included to releasably attach the cuff to the patient's limb. The tab is provided with a visible indicium which indicates the proper degree of overlap of the ends of the cuff when the latter is affixed to the patient's limb. The cuff may be used by only one patient, and may be discarded when the patient is finished with it. The cuff is provided with a one-piece slip luer fitting which includes a flange disposed within the chamber, and an annular tube projecting through an outer component of the cuff. The slip luer flange is adhered to the outer cuff component, and the annular tube includes a tapered part which is operative to provide a sealed joint with a complementary luer fitting on a blood pressure monitor inflation/deflation line, thereby eliminating the necessity of a separate hose component on the cuff.

10 Claims, 1 Drawing Sheet

U.S. Patent    Oct. 21, 1997    5,678,558
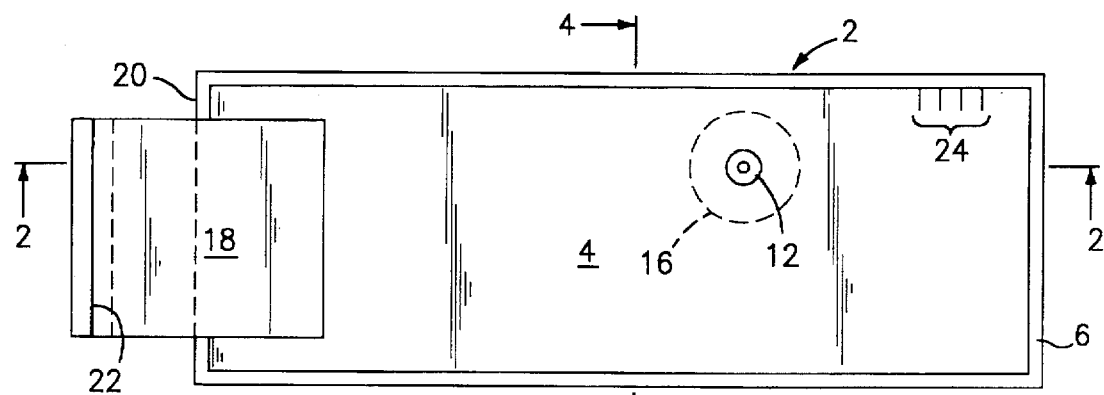
FIG. 1
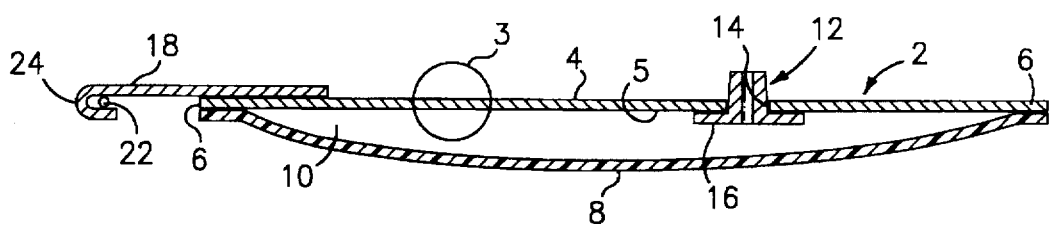
FIG. 2
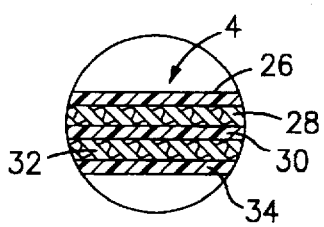
FIG. 3
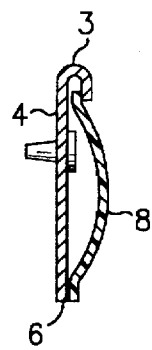   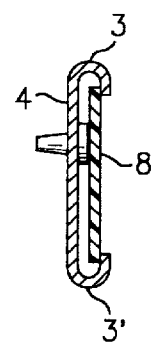
FIG. 4    FIG. 5
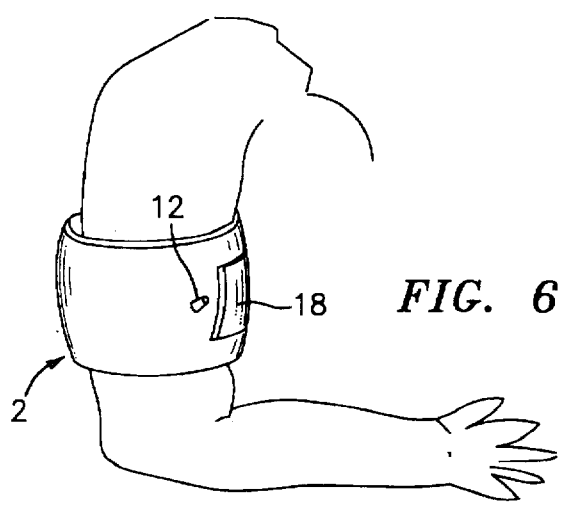
FIG. 6

DISPOSABLE BLOOD PRESSURE CUFF

This is a continuation of U.S. Ser. No. 08/300,396, filed Sep. 2, 1994, now U.S. Pat. No. 5,511,552.

TECHNICAL FIELD

This invention relates to an inflatable blood pressure cuff and more particularly to a cuff which is formed from a composite which includes an outer non-stretchable paper component, and an inner elastic thermoplastic material component which contacts the patient, which cuff may be discarded and safely disposed of after use by a patient.

BACKGROUND ART

Inflatable blood pressure cuffs are typically composite structures formed from vinyls, nylon, rubber and typically include a hook and loop type of closure. The various material layers in the cuff are stitched or otherwise bonded together so as to form the inner inflatable bladder part of the cuff, and the outer constricting part of the cuff. The cuff must be capable of being inflated on the patient without undergoing undue radial expansion. The aforesaid cuffs are used on the entire patient population, and are not typically designed for use on only one patient. These cuffs are relatively expensive and are not intended to be discarded after use on a particular patient. Cuffs have been designed which are intended to be used on only a single patient, but their cost has caused them to be reused on other patients. It would be desirable to have a sufficiently inexpensive blood pressure cuff that is designed for use on only one patient, and that can be economically discarded after use on the patient.

DISCLOSURE OF THE INVENTION

This invention relates to an inexpensive inflatable blood pressure cuff which is intended to be used on only one patient and which may be economically discarded and safely disposed of after it has been used. Disposal of the cuff after a single patient's use eliminates the risk of the cuff contaminating other patients or health care givers who would otherwise also use the cuff. Single patient use is especially important in cases where the cuff is being used in emergency situations, or is being used on patients who have infectious diseases that might be transmitted to others by the cuff.

The cuff of this invention is formed as a composite structure which includes an outer paper component for strength, and an inner elastic resinous component for the necessary arterial occluding capability. The paper component is formed from an essentially non-stretchable paper such as paper marketed by James River Corporation under the brand name Riegel, grades GP23XD, GP23XE, GR23XG or GP25BL, or an equivalently non-stretchable paper. The paper component will preferably have inner and outer surfaces which are provided with a thermoplastic material layer so as to provide heat-sealable surfaces and/or adhesive-receptive surfaces on the outer component. The outer paper component will provide enhanced printing capabilities on the outer surface of the cuff. Existing blood pressure cuffs are screen printed, which provides very limited print quality. The inner portion of the cuff will be formed by the elastic thermoplastic material. With the conjoined outer paper component and inner thermoplastic component, the cuff, when inflated, will not expand outwardly, but it will expand inwardly so as to appropriately occlude a patient's appendage. The cuff will also include a closure member which is preferably an adhesive tape strip attached to one edge of the outer surface of the cuff. The closure strip can be equipped with a visible indicium that provides an indication of the proper degree of overlap of the ends of the cuff when affixed to the patient.

The cuff of this invention can be fabricated by heat sealing or otherwise securing the edges of the inner elastic and outer constricting components together so as to form the cuff with an internally flexible and outwardly constricted inflatable chamber. A male luer fitting will be provided in the outer component for attachment to an inflation/deflation hose. After patient use, the cuff can be safely incinerated or recycled without producing any harmful toxins.

It is therefore an object of this invention to provide a disposable inflatable blood pressure cuff which is intended for use by only one patient.

It is a further object of this invention to provide a cuff of the character described which is inexpensive to fabricate.

It is another object of this invention to provide a cuff of the character described which can be disposed of by incinerating, or can be recycled without producing any harmful toxins.

These and other objects and advantages of the invention will become more readily apparent from the following detailed description of the invention when taken in conjunction with the accompanying drawings in which:

BRIEF DESCRIPTION OF THE DRAWINGS

FIG. 1 is a plan view of an embodiment of the cuff of this invention;

FIG. 2 is a sectional view of the cuff taken along lines 2—2 of FIG. 1;

FIG. 3 is an enlarged fragmented sectional view of the outer component of the cuff showing the various laminations included therein;

FIG. 4 is a sectional view taken along line 4—4 of FIG. 1 showing an alternate way of joining the inner and outer components of the cuff together;

FIG. 5 is a sectional view similar to FIG. 4 but showing yet another way of joining the inner and outer components of the cuff together; and FIG. 6 illustrates the manner of use of the cuff on a patient's arm.

DETAILED DESCRIPTION OF THE INVENTION

Referring now to the drawings, there is shown in FIGS. 1 and 2 a preferred embodiment of an inflatable blood pressure cuff formed in accordance with this invention. The cuff is denoted generally by the numeral 2 and includes an outer component 4 which provides the necessary appendage constriction strength and has a primary component layer which is formed from a laminate that includes a layer of non-stretchable paper. The outer component 4 is sealed at its peripheral edges 6 to an inner elastic component 8 which is formed from an elastic resinous material such as polyethylene, or the like. The outer and inner components 4 and 8 combine to form an internal cavity 10 which can be inflated so as to expand the elastic component 8 against the patient's appendage to occlude blood flow in the appendage sufficiently to enable oscillometric or auscultatory blood pressure measurements to be made in a known manner. A male luer fitting 12 is fitted into an opening 14 in the outer component 4 and is operable to telescopingly connect directly with a mating luer fitting on an inflation/deflation hose on an automated blood pressure monitor (not shown)

during inflation and deflation of the cuff 2. The cuff-mounted luer fitting 12 eliminates the need for a separate hose component on the cuff, and the separate luer sub-component commonly used in the prior art, since the fitting 12 may be coupled directly with the monitor hose mating luer fitting. The luer fitting 12 has an integral flange 16 which is bonded to the inner surface 5 of the outer component 4, as will be explained hereinafter. The cuff 2 has a closure component 18 which extends beyond one edge 20 of the cuff 2 and which is adhered to the outer surface of the outer cuff component 4. The closure component 18 can advantageously be formed from a strip of contact adhesive tape, and may include an indicium 22 such as a visible stripe which can serve as an indicator for alignment with a series of indicia 24 on the opposite side of the cuff 2 which indicate a recommended range of cuff overlap for providing proper cuff fittings. The distal edge of the closure 18 can be folded underneath as at 24 (see FIG. 2) to provide a non-tacky area for manual gripping purposes. A release strip (not shown) can also be provided to cover the tacky surface of the closure 18.

Referring now to FIG. 3, there is shown a suitable lamination sequence for the outer cuff component 4. The outermost layer 26 of the outer cuff component 4 is preferably polypropylene which is applied to the underlying layer 28, which is the non-stretchable paper, so as to provide a smooth surface for the closure tape 18 or other closure to be adhered to, as well as protecting any printing on the underlying paper layer. A polyethylene layer 30 is disposed on the inner surface of the paper layer 28 and a metallic foil layer 32 (preferably aluminum foil) is heat sealed onto the polyethylene layer 30. The innermost layer 34 of the outer cuff component 4 is preferably polyethylene. The polyethylene layer 34 allows the outer and inner cuff components 4 and 8 to be edge-bonded to each other to form the sealed internal cavity 10 in the cuff 2. The polyethylene layer 34 also allows the luer flange 16 to be heat seal-bonded to the inner surface 5 of the outer cuff component 4. The inner cuff component 8 is preferably polyethylene and it may have a patient-comfort layer on it, such as cotton flocking, foam, or the like, which comfort layer contacts the patient's skin.

Referring now to FIGS. 4 and 5, there are shown several different variations in the cuff-wise longitudinal peripheral edge seals between the outer cuff component 4 and the inner cuff component 8. In the embodiment shown in FIG. 4, one edge 3 of the outer cuff component 4 is folded over and sealed to the adjacent edge of the inner cuff component 8, while the opposite edge 6 is formed with a simple face-to-face seal application. In the embodiment shown in FIG. 5, both edges of the outer cuff component 4 are folded over and sealed to the adjacent edges of the inner cuff component 8. The folded-over versions are operative to round off the edges of the cuff.

FIG. 6 shows how the cuff 2 is applied to the arm of a patient, with the closure tape 18 being overlapped on the cuff 2, and with the luer fitting 12 rendered available for securement to a complementary luer fitting on the monitor inflation/deflation hose.

The aforesaid description of the invention provides information as to one embodiment of the cuff of this invention, however, other cuff constructions are also contemplated by the invention. For example, the outer layer of the cuff could be formed from the following sequences of air impermeable layers, as seen from the inside to the outside of the cuff. The following sequences are illustrative of material laminate sequences that could be used to form the cuff of this invention:

a) polyethylene/aluminum foil/polyethylene/paper/polyester;

b) polyethylene/aluminum foil/polyethylene/paper/polyethylene;

c) polyethylene/aluminum foil/polyethylene/paper;

d) polyethylene/paper/polypropylene;

e) polyethylene/paper;

f) "SURLYN"ionomer resin/aluminum foil/polyethylene/paper/polypropylene;

g) "SURLYN"ionomer resin/aluminum foil/polyethylene/paper/polyester;

h) "SURLYN"ionomer resin/aluminum foil/polyethylene/paper/polyethylene;

i) "SURLYN"ionomer resin/aluminum foil/polyethylene/paper;

j) polyethylene/paper/polyester;

k) "SURLYN"ionomer resin/paper/polypropylene;

l) "SURLYN"ionomer resin/paper/polyester;

m) "SURLYN"ionomer resin/paper/polyethylene;

n) polyethylene/paper/polyester/polyethylene;

o) "SURLYN"ionomer resin/paper; and p) heat-seal coating/paper.

The above listing is intended to be illustrative of possible combinations, and is not an exhaustive listing.

"Surlyn" is a trademark of DuPont de Nemours, E. I. & Co. for ionomer resins. Suitable heat-seal coatings include polyethylene, "SURLYN"ionomer resin, polyurethane, ethyl vinyl acetate (EVA), ethyl acrylic acid, ethyl methyl acrylic acid, and the like.

The aforesaid layers can be bonded together by heat sealing, radio frequency bonding, glueing, or the like. Instead of using an adhesive tape closure, the cuff could utilize a hook and loop fastener adhered to the outer surface of the cuff.

The cuff is primarily sufficiently inexpensive so as to be discardable after use by a single patient, however, it is sufficiently durable so as to be capable of multiple uses if so required.

Since many changes and variations of the disclosed embodiments of the invention may be made without departing from the inventive concept, it is not intended to limit the invention otherwise than as required by the appended claims.

What is claimed is:

1. An inflatable blood pressure cuff comprising:
   a) an outer air-impervious component which includes an essentially non-stretchable paper layer that resists outward expansion when the cuff is inflated;
   b) an inner elastic resin component which combines with said outer component to form an internal expandable chamber, said resin component being operable to compress a patient's appendage when said expandable chamber is inflated, said inner and outer components having joined edges which are operable to seal all edges of said expandable chamber; and
   c) a fitting which is adapted to be connected to an inflation/deflation hose, said fitting allowing selected inflation and deflation of the cuff.

2. The cuff of claim 1 wherein said inner component is formed from polyethylene, said polyethylene inner component including peripheral edges which are sealed to corresponding peripheral edges of said outer component to close said chamber.

3. The cuff of claim 2 wherein said peripheral edges on said inner component are sealed to surfaces of said outer component which face said internal chamber.

4. The cuff of claim 2 wherein said peripheral edges on said inner component are sealed to surfaces of said outer component which face away from said internal chamber.

5. The cuff of claim 2 wherein said peripheral edges on said inner component are sealed to first surfaces of said outer component which face toward said internal chamber, and are sealed to second surfaces of said outer component which face away from said internal chamber.

6. The cuff of claim 1 further including a closure adhered to an outer surface of said outer component, said closure extending beyond an edge of the cuff to provide means for securing the cuff on an appendage of a patient.

7. The cuff of claim 6 wherein said closure is an adhesive tape.

8. The cuff of claim 7 wherein said adhesive tape includes visible indicium for determining a proper extent of overlap for the cuff when the latter is applied to the patient's appendage.

9. The cuff of claim 1 wherein said outer and inner components are formed from materials which can be disposed of by incineration without producing toxic by products.

10. An inflatable blood pressure cuff which may be used by a single patient and safely disposed of thereafter, said cuff comprising:

a) an inner elastic resin component, said inner component being operable to compress a patient's appendage when said cuff is inflated;

b) an outer air-impervious component which combines with said inner component to form an internal expandable cuff inflation chamber, said outer component comprising:

i) a first layer of bondable material facing said inflation chamber, said bondable layer having edges that are sealed to said inner elastic resin component to seal said cuff inflation chamber from ambient surroundings;

ii) an essentially non-stretchable paper layer secured to and overlying said first layer, said paper layer being operable to resist outward expansion when the cuff is inflated; and c) a fitting which is adapted to be connected to an inflation/deflation hose, said fitting allowing selected inflation and deflation of the cuff.

* * * * *